(12) United States Patent
Koerner et al.

(10) Patent No.: US 7,374,553 B2
(45) Date of Patent: May 20, 2008

(54) SYSTEM FOR BI-DIRECTIONALLY CONTROLLING THE CRYO-TIP OF A CRYOABLATION CATHETER

(75) Inventors: Richard J. Koerner, San Diego, CA (US); David J. Lentz, La Jolla, CA (US); Joseph A. O'Donnell, Escondido, CA (US); Alvin B. Salinas, San Marcos, CA (US)

(73) Assignee: Cryocor, Inc., San Diego, CA (US)

( * ) Notice: Subject to any disclaimer, the term of this patent is extended or adjusted under 35 U.S.C. 154(b) by 590 days.

(21) Appl. No.: 10/876,306

(22) Filed: Jun. 24, 2004

(65) Prior Publication Data
US 2005/0288656 A1 Dec. 29, 2005

(51) Int. Cl.
*A61M 31/00* (2006.01)
(52) U.S. Cl. .................................... 604/95.04
(58) Field of Classification Search ............... 600/147, 600/148, 149, 434, 146; 604/264, 524, 525, 604/526, 528, 530, 95.05, 95.04; 606/21
See application file for complete search history.

(56) References Cited

U.S. PATENT DOCUMENTS

| | | | |
|---|---|---|---|
| 1,060,665 A | 5/1913 | Bell | |
| 3,605,725 A | 9/1971 | Bentov | |
| 4,456,017 A | 6/1984 | Miles | |
| 4,586,923 A | 5/1986 | Gould et al. | |
| 4,813,434 A | 3/1989 | Buchbinder et al. | |
| 4,815,478 A | 3/1989 | Buchbinder et al. | |
| 4,886,067 A | 12/1989 | Palermo | |
| 4,960,134 A | 10/1990 | Webster, Jr. | |
| 4,960,411 A | 10/1990 | Buchbinder | |
| 4,976,688 A | 12/1990 | Rosenblum | |
| 5,037,391 A | 8/1991 | Hammerslag et al. | |
| 5,042,985 A | 8/1991 | Elliott et al. | |
| 5,108,368 A | 4/1992 | Hammerslag et al. | |
| 5,114,414 A | 5/1992 | Buchbinder | |
| 5,125,895 A | 6/1992 | Buchbinder et al. | |
| 5,190,050 A | 3/1993 | Nitzsche | |
| 5,242,441 A | 9/1993 | Avitall | |
| 5,318,525 A | 6/1994 | West et al. | |
| 5,322,064 A * | 6/1994 | Lundquist | 600/381 |
| 5,330,466 A | 7/1994 | Imran | |
| 5,334,145 A | 8/1994 | Lundquist et al. | |
| 5,368,564 A | 11/1994 | Savage | |
| 5,507,725 A | 4/1996 | Savage et al. | |

(Continued)

*Primary Examiner*—Nicholas D. Lucchesi
*Assistant Examiner*—Christopher D Koharski
(74) *Attorney, Agent, or Firm*—Nydegger & Associates

(57) ABSTRACT

A bi-directional system for actively deflecting the distal tip of a catheter includes a reconfigurable tube that is positioned proximal to the catheter's distal tip. The tube is formed with slits that are arranged to allow the tube to be transformed from a relaxed, cylindrical configuration to a plurality of deflected configurations. First and second pull wires are provided, with each wire having a respective distal end that is attached to the distal end of the tube. Each wire extends to a catheter handle where it is attached to a respective reel. The reels can be rotated, back and forth, to selectively deflect or relax the tube. To ensure a smooth recovery after a relatively large deflection, a mechanism is disclosed for delaying an application of tension on one of the pull wires until at least a portion of any tension on the other pull wire is released.

14 Claims, 6 Drawing Sheets

U.S. PATENT DOCUMENTS

| | | |
|---|---|---|
| 5,656,030 A | 8/1997 | Hunjan et al. |
| 5,667,476 A * | 9/1997 | Frassica et al. ............ 600/149 |
| 5,715,817 A | 2/1998 | Stevens-Wright et al. |
| 5,906,590 A | 5/1999 | Hunjan et al. |
| 5,928,191 A | 7/1999 | Houser et al. |
| 5,944,689 A | 8/1999 | Houser et al. |
| 6,013,052 A | 1/2000 | Durman et al. |
| 6,066,125 A | 5/2000 | Webster, Jr. |
| 6,106,518 A | 8/2000 | Wittenberger et al. |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,254,568 B1 | 7/2001 | Ponzi |
| 6,267,746 B1 | 7/2001 | Bumbalough |
| 6,319,248 B1 | 11/2001 | Nahon |
| 6,332,880 B1 | 12/2001 | Yang et al. |
| 6,346,099 B1 | 2/2002 | Altman |
| 6,413,234 B1 | 7/2002 | Thompson et al. |
| 6,440,126 B1 | 8/2002 | Abboud et al. |
| 6,468,260 B1 | 10/2002 | Bumbalough et al. |
| 6,485,455 B1 | 11/2002 | Thompson et al. |
| 6,500,167 B1 | 12/2002 | Webster, Jr. |
| 6,522,933 B2 | 2/2003 | Nguyen |
| 6,540,725 B1 | 4/2003 | Ponzi |
| 6,551,271 B2 | 4/2003 | Nguyen |
| 6,569,114 B2 | 5/2003 | Ponzi et al. |
| 6,571,131 B1 | 5/2003 | Nguyen |
| 6,579,278 B1 | 6/2003 | Bencini |
| 6,585,717 B1 | 7/2003 | Wittenberger et al. |
| 6,585,718 B2 | 7/2003 | Hayzelden et al. |
| 6,602,278 B1 | 8/2003 | Thompson et al. |
| 6,605,086 B2 | 8/2003 | Hayzelden et al. |
| 6,607,505 B1 | 8/2003 | Thompson et al. |
| 6,610,058 B2 | 8/2003 | Flores |
| 2001/0025075 A1 | 9/2001 | Smith et al. |
| 2002/0025998 A1 | 2/2002 | McCullough et al. |

* cited by examiner

SYSTEM FOR BI-DIRECTIONALLY CONTROLLING THE CRYO-TIP OF A CRYOABLATION CATHETER

FIELD OF THE INVENTION

The present invention pertains generally to systems and methods for actively deflecting a distal portion of a catheter while the distal portion is positioned within a body conduit. More particularly, the present invention pertains to a bi-directional system for deflecting the distal portion of a catheter. The present invention is particularly, but not exclusively, useful as a system for bi-directionally controlling the cryo-tip of a cryoablation catheter.

BACKGROUND OF THE INVENTION

Atrial fibrillation is an irregular heart rhythm that adversely affects approximately 2.5 million people in the United States. It is believed that at least one-third of all atrial fibrillation originates near the ostium of the pulmonary veins. Anatomically, two pairs of pulmonary veins are connected to the left atrium of the heart with each pair delivering blood to the heart from one of the patient's lungs.

It is further believed that the optimal technique to treat atrial fibrillation is to create circumferential lesions around the ostia where a pulmonary vein connects with the left atrium. More specifically, the goal is to ablate tissue to form a conduction block to thereby prohibit the transmission of irregular electrical signals that can cause an arrhythmia. To be effective, the conduction block must completely block irregular signals and this often requires the ablation of a relatively deep, uniform lesion. In some cases, more than one pulmonary vein must be treated to cure an arrhythmia.

To create circumferential lesions around the ostia using cryoablation, a typical procedure involves contacting tissue around the periphery of an ostium with a cryo-element and then cooling the cryo-element to ablate the contacted tissue. In some cases, the cryo-element can be hoop shaped allowing for a single-contact cryoablation. In other cases, a cryo-element that is arcuate, partially hoop shaped or dome shaped can be used. For such cryo-elements, multiple, successive contacts between the cryo-element and tissue are typically required. More specifically, these procedures require the cryo-element to be successively moved around the ostia to create a continuous ablation band.

For all of these types of cryo-elements, it is necessary to articulate the distal end of the catheter with great accuracy to aim and direct the cryo-element into contact with the targeted tissue. Moreover, this manipulation typically must be performed within a relatively limited space (e.g. the left atrium). For this purpose, it is desirable to be able to deflect the distal end of the catheter in more than one direction. With bi-directional capability, the distal end of the catheter can be deflected in a first direction (e.g. upward) to treat a first pulmonary vein, for example, and subsequently deflected in a second direction (e.g. downward) to treat a second vein. Furthermore, the ability to deflect the distal end of the catheter at relatively large deflection angles can potentially simplify and quicken many procedures.

In a typical bi-directional deflection system, a first pull wire is used to deflect the distal catheter tip in a first direction and second pull wire is provided to deflect the distal catheter tip in a second direction, opposite the first direction. For these conventional systems, a change in deflection from one direction to another can be problematic. For instance, when the tip is deflected a relatively small amount in the first direction, the second pull wire can typically be retracted to first straighten the catheter tip, and then deflect the tip in the second direction. However, when the deflection of the distal tip in the first direction is relatively large (e.g. ninety to one hundred eighty degrees or more), retraction of the second pull wire does not necessarily operate to smoothly recover the deflection and straighten the tip. Instead, for conventional bi-directional systems, retraction of the second wire can actually cause further deflection in the first direction and may prevent a deflection recover when the tension in the first wire is released.

In light of the above, it is an object of the present invention to provide a bi-directional system for actively deflecting a distal portion of a catheter while the distal portion is positioned within a body conduit. It is another object of the present invention to provide a system for bi-directionally controlling the cryo-tip of a cryoablation catheter that transitions from one direction to another with the operation of a single control knob. It is yet another object of the present invention to provide a system for bi-directionally controlling the cryo-tip of a cryoablation catheter that actively controls the amount of tip deflection in both directions and can hold the deflected cryo-tip in place. Yet another object of the present invention is to provide a bi-direction control system which is easy to use, relatively simple to implement, and comparatively cost effective.

SUMMARY OF THE INVENTION

The present invention is directed to a bi-directional system for actively deflecting the distal portion of a catheter. More specifically, the system is typically designed to deflect the catheter's distal portion in either of two directions. Thus, the distal portion may be deflected in a first direction from a relaxed (i.e. straight) configuration, and thereafter smoothly deflected in a second direction that is coplanar and opposite the first direction. Applications of the bi-directional system can include: 1) steering the distal tip of a catheter through a body conduit during advancement of the distal tip to an internal target location; and 2) placing the distal tip in one or more preselected orientations at the target location.

In greater structural detail, the bi-directional system includes an elongated catheter body having a proximal portion, and the distal portion mentioned above. In this combination, the distal portion is formed with a lumen. Also, a tube is disposed in the lumen and located proximal to the catheter's distal tip. This tube, which is typically made of a metal, has a proximal end and a distal end and it is formed with a plurality of slits that are arranged along the length of the tube. The purpose of these slits is to allow the tube to be transformed from a relaxed configuration, in which the tube is substantially cylindrical and defines a tube axis, into a plurality of deflected configurations. More specifically, in the deflected configurations, the distal end of the tube is displaced from the tube axis in either a first direction or a second direction that is coplanar and opposite the first direction.

To deflect the tube in a manner as suggested above, the system includes first and second pull wires. Each of these pull wires has a respective distal end that is attached to the distal end of the tube. From their respective attachment points, each pull wire extends proximally through the tube to a housing on the handle of the catheter. At the handle, a pair of reels (i.e. a clockwise (CW) reel and a counter-clockwise (CCW) reel) are positioned in the handle housing and mounted on the catheter with each reel being rotatable relative to the housing about a common axis of rotation. The proximal end of one pull wire (e.g. the first wire) is attached to the circumference of the CW reel and the proximal end of other pull wire (e.g. the second wire) is attached to the circumference of the CCW reel. With this cooperation of structure, the CW reel can be rotated back and forth to selectively pull and release the first pull wire. Specifically, a pull on the first wire deflects the distal end of the tube in the first direction, while a release of the first wire relaxes the tube into its initial cylindrical configuration. In a similar manner, back and forth rotations of the CCW reel result in the distal end of the tube being deflected in the second direction or relaxed into the initial cylindrical configuration.

In addition to the CW and CCW reels, the system further includes a drive cog that is mounted on the handle housing for rotation about the axis of rotation in either a first or second rotation direction. Functionally, when the drive cog is rotated in the first rotation direction, it engages and rotates the CW reel. On the other hand, when the drive cog is rotated in the second rotation direction, it engages and rotates the CCW reel. Each of the reels and the drive cog are stacked along the rotation axis and are positioned inside the handle housing opposite a user operable turn knob. Specifically, the turn knob is positioned outside the handle housing with a friction washer interposed between the housing and the knob. With this combination, a screw can then be used to clamp the knob toward the drive cog at a preselected clamping pressure. As a consequence, the friction washer and the wall of the housing are sandwiched between the turn knob and drive cog. As intended for this structural arrangement, the user can rotate the turn knob to selectively pull on either the first or the second pull wires. Also, the friction washer then "locks" the knob in place after a preselected rotation. This allows the operator to release their hand from the knob while maintaining a preselected tip deflection.

In one implementation of the deflection system, a guiding mechanism is provided to maintain both the first and second pull wires adjacent to the inner wall of the tube during a deflection of the tube. For example, this guiding mechanism can include a plurality of indentations that are formed in the tube to hold the pull wires against the inner wall while allowing the pull wires to pass freely through each indentation. Specifically, each indentation can be formed from a portion of the tube wall that is located between a pair of axially adjacent slits in the wall. More specifically, each indentation protrudes radially inward toward the center of the tube to form a passageway that can be used to thread one of the pull wires through the indentation As intended for the present invention, a plurality of such indentations can be formed in an axial direction along the tube to concertedly hold a pull wire.

In another aspect of the invention, the system includes a mechanism that is operable on the pull wires for delaying an application of tension on one of the pull wires until at least a portion of any tension on the other pull wire is released. This delay allows for the recovery of large deflections. For the case where CW and CCW reels and a drive cog are used to control the pull wires, the delay mechanism can be implemented by the establishment of a gap between the cog and the reels. Specifically, when the tube is in a relaxed state and there is no tension on either pull wire, the cog is centered between the two reels with a gap between the cog and the CW reel and an equal size gap between the cog and the CCW reel. With properly sized gaps, only one wire at a time can be placed in tension, resulting in the smooth recovery of relatively large deflections.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
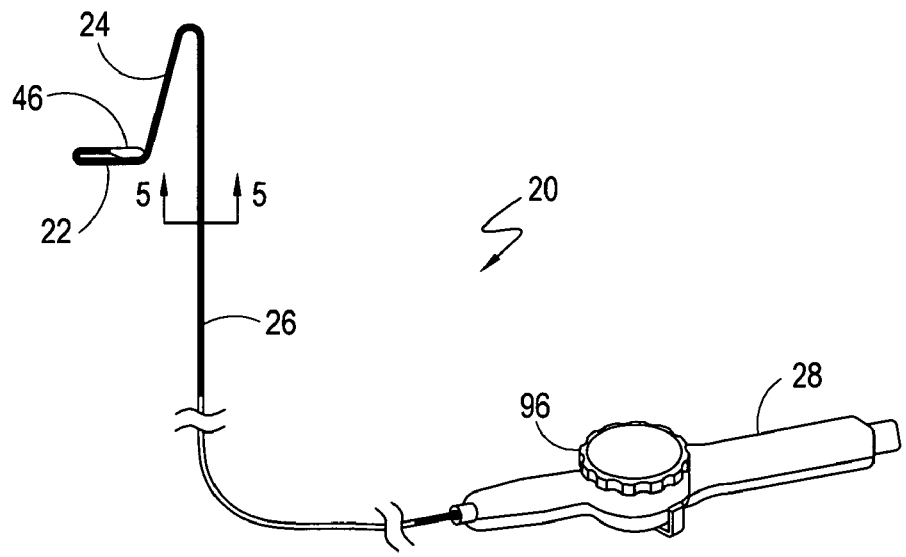
FIG. 1 is a perspective view of a cryo-catheter having a bi-directional control system and a system for deflecting a section of the cryo-catheter into a hooped configuration.

Referring initially to FIG. 1, a cryo-catheter for cryoablating a lesion in a body conduit of a patient is shown and generally designated 20. As indicated in FIG. 1, the cryo-catheter 20 can be manipulated into different configurations and orientations. To do this, the cryo-catheter 20 includes a system for deflecting a section 22 of the cryo-catheter 20 into a hoop configuration, as shown. It also includes a bi-directional control system for deflecting a section 24 of the cryo-catheter 20 in both a first direction and a second direction that is substantially coplanar and opposite the first direction. FIG. 1 further shows that the cryo-catheter 20 includes an elongated catheter body 26 that extends distally from a catheter handle 28. Although these deflecting systems are shown and disclosed herein as being part of a cryo-catheter 20, those skilled in the pertinent art will appreciate that these systems can be used as well in other types of catheters where bi-directional control or an actively produced hoop shaped configuration are desirable.

Figure 2:
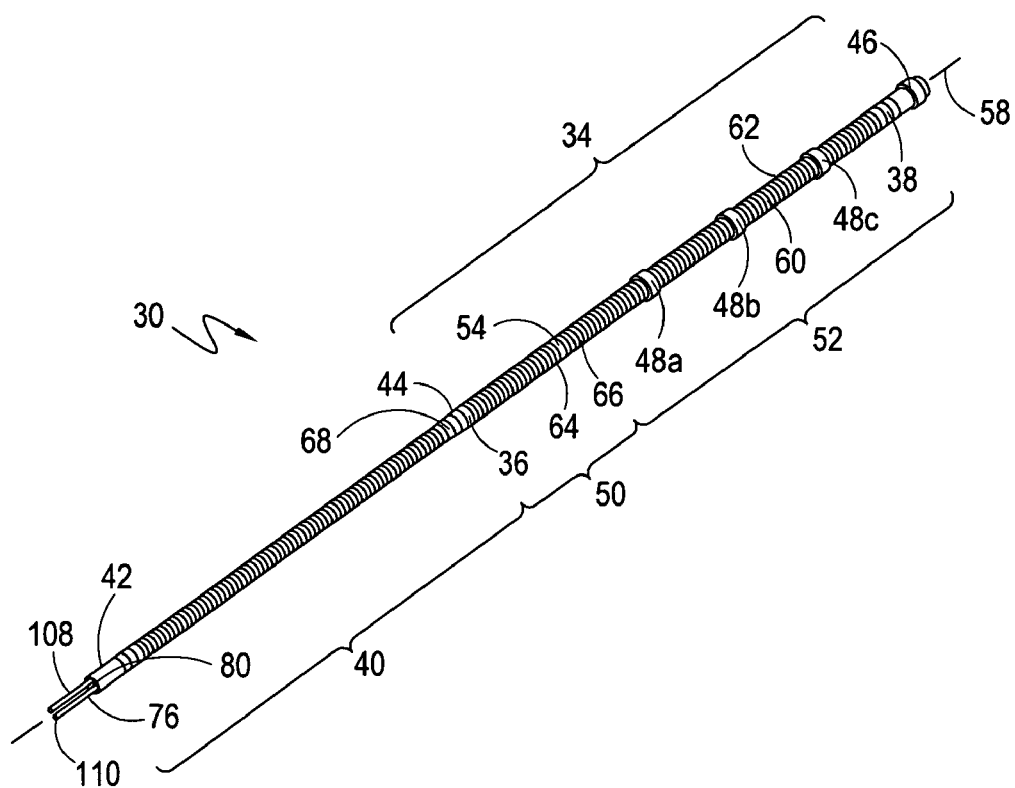
FIG. 2 is a perspective view of a distal portion of the cryo-catheter, shown with the flexible catheter jacket removed to reveal the internal structure of the catheter.

Referring now to FIG. 2, a distal portion of the cryo-catheter 20, generally designated 30, is shown with the outer catheter body 26 removed to reveal internal components. As shown, the cryo-catheter 20 includes a distal tube 34 having a proximal end 36 and a distal end 38, a proximal tube 40 having a proximal end 42 and a distal end 44, and a cryo-tip 46 that is mounted on the distal tube 34 at its distal end 38. For the embodiment shown, the cryo-catheter 20 also includes three EKG band electrodes 48a-c. FIG. 2 further shows that the distal tube 34 includes two distinct sections 50, 52, with section 50 extending from the proximal end 36 of the distal tube 34 to a section distal end 54 and section 52 extending from the distal end 54 of section 50 to the distal end 38 of the distal tube 34.

Figure 3:
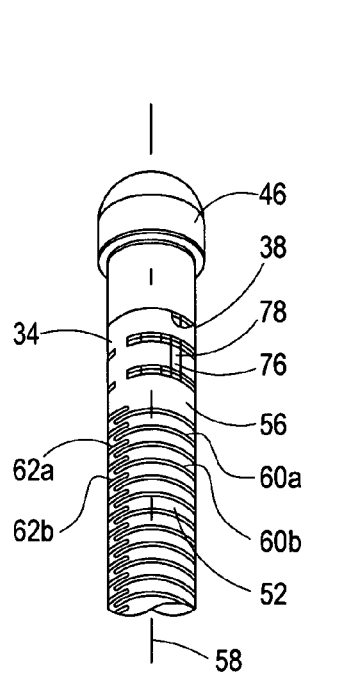
FIG. 3 is an enlarged, perspective view of the distal tip of the cryo-catheter.

Cross-referencing FIGS. 2 and 3, it can be seen that the distal tube 34 has a wall 56 and defines a tube axis 58. Section 52 of the distal tube 34 further includes a plurality of first slits, of which exemplary first slits 60a,b have been labeled, which are cut through the wall 56 and oriented in respective planes that are substantially perpendicular to the tube axis 58. As further shown, each first slit 60a,b extends azimuthally in an arc partway around the axis 58 and each has a center and a substantially same arc length, which is typically slightly greater than one-hundred eighty degrees. Further, it can be seen that the respective centers of these first slits 60 are aligned with each other in a first centerline that is oriented substantially parallel to the tube axis 58. For the embodiment shown, section 52 of the distal tube 34 is also formed with a plurality of second slits, of which exemplary second slits 62a,b have been labeled, and which, like the first slits 60a,b, establish a second centerline that is substantially parallel to the tube axis 58. Typically, the second slits 62a,b are cut into the tube wall 56 such that the second centerline is diametrically opposed to the first centerline (i.e. located one-hundred eighty degrees around the circumference of the distal tube 34 from the first centerline). With this arrangement of first slits 60 and second slits 62, the section 52 of the distal tube 34 can be transformed between a first, relaxed configuration wherein section 52 is substantially cylindrical shaped (as shown in FIGS. 2 and 3) and a second, deflected configuration wherein section 52 of the distal tube 34 is substantially hoop shaped (hoop shown in FIG. 1). For the cryo-catheter 20, the distal tube 34 is typically made of a thin walled stainless steel material (e.g. 304 alloy) that has been cut with a laser to form the slits 60, 62 described above. A more detailed description of the tube 34 can be found in co-pending, co-owned U.S. patent application Ser. No. 10/774,665, filed Feb. 9, 2004, which is hereby incorporated by reference in its entirety herein.

Continuing with FIGS. 2 and 3, the wall 56 of the distal tube 34 within the section 50 is formed with a plurality of first slits 64 and a plurality of second slits 66 which are cut through the wall 56 and oriented in respective planes that are substantially perpendicular to the tube axis 58. As further shown, each slit 64, 66 extends azimuthally in an arc partway around the tube axis 58 and each has a center and a substantially same arc length, which is typically slightly greater than one-hundred eighty degrees. Further, the respective centers of the first slits 64 are aligned with each other in a first centerline, the respective centers of the second slits 66 are aligned with each other in a second centerline and both first and second centerlines are oriented substantially parallel to the tube axis 58. For the section 50, the second centerline is diametrically opposed to the first centerline.

FIG. 2 further shows that the first slits 64 of section 50 are azimuthally displaced from the first slits 60 of section 52 by approximately ninety degrees. Thus, the first centerline of section 50 is azimuthally displaced from the first centerline of section 52 by approximately ninety degrees. Similarly, the second slits 66 of section 50 are azimuthally displaced from the second slits 62 of section 52 by approximately ninety degrees. With this arrangement of first slits 64 and second slits 66, the section 50 of the distal tube 34 can be transformed between a first, relaxed configuration wherein section 50 is substantially cylindrical shaped (as shown in FIGS. 2 and 3) and a second, deflected configuration wherein section 50 of the distal tube 34 is curved to establish a transition section between the hoop and the bi-directional section (see FIG. 1).

FIG. 2 also shows that the proximal tube 40 has a wall 68 and for the cryo-catheter 20, the proximal tube 40 is centered along the tube axis 58. Cross-referencing FIGS. 2 and 4 it can be seen that the wall 68 of the proximal tube 40 is formed with a plurality of first slits 70 and a plurality of second slits 72 which are cut through the wall 68 and oriented in respective planes that are substantially perpendicular to the tube axis 58. As further shown, each slit 70, 72 extends azimuthally in an arc partway around the tube axis 58 and each has a center and a substantially same arc length, which is typically slightly greater than one-hundred eighty degrees. Further, the respective centers of the first slits 70 are aligned with each other in a first centerline, the respective centers of the second slits 72 are aligned with each other in a second centerline and both first and second centerlines are oriented substantially parallel to the tube axis 58. For the proximal tube 40, the second centerline is diametrically opposed to the first centerline.

Figure 4:
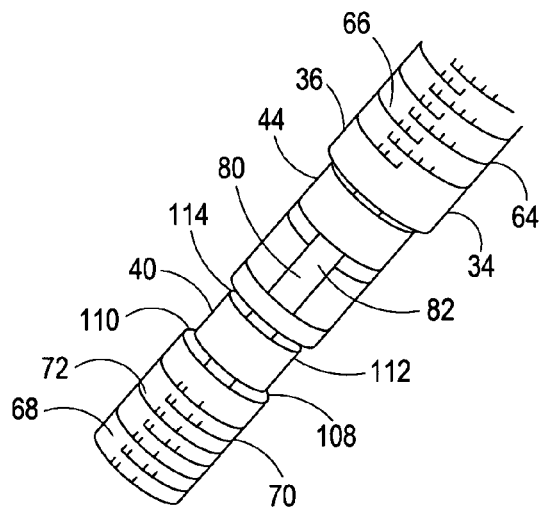
FIG. 4 is an enlarged, perspective view of the junction between the distal tube and the proximal tube of the catheter.

Continuing with cross-reference to FIGS. 2 and 4, it can be seen that the distal end 44 of the proximal tube 40 is attached to the proximal end 36 of the distal tube 34. As shown, the proximal tube 40 has a diameter that is slightly smaller than the diameter of the distal tube 34 allowing the distal end 44 of the proximal tube 40 to be inserted into the proximal end 36 of the distal tube 34 and attached thereto. Typically, the tubes 34, 40 are welded or bonded together. FIGS. 2 and 4 also show that the tube 34 is attached to the tube 40 with the centerline of the first slits 70 aligned with the center line of the first slits 64 of section 50 of the distal tube 34. Similarly, it can be seen that the tube 34 is attached to the tube 40 with the centerline of the second slits 72 aligned with the center line of the second slits 66 of section 50 of the distal tube 34.

Cross-referencing FIG. 1 with FIG. 3, it can be appreciated that the distal tube 34, proximal tube 40 and the proximal portion of the cryo-tip 46 are all disposed in the lumen 74 (see FIG. 5) of the distal portion of the catheter body 26. For the cryo-catheter 20, the distal portion of the catheter body 26 is made of a flexible, polymeric material which is bonded to the cryo-tip 46. On the other hand, the proximal portion of the catheter body 26 which extends from the handle 28 to the distal portion of the catheter body 26 is typically made of a polymeric material which is more rigid than the distal portion of the catheter body 26. For some implementations, the catheter body 26 within the hoop section 22 is made of a polymeric material filled with a conductive material to enhance the conductivity of the catheter body 26 in the hoop section 22. For example, the composite material typically includes between approximately ten weight percent and thirty weight percent (10 wt. %-30 wt. %) of filler material with the balance being polymeric matrix material. Suitable filler materials can include, but are not limited to, metals, metal alloys, ceramics, carbon and combinations thereof.

To deflect the section 22 (see FIG. 1) into a hoop shaped configuration, the cryo-catheter 20 includes a deflection wire 76 (see FIG. 5) having a distal end 78 that is attached to the distal end 38 of the distal tube 34, as shown in FIG. 3. For some embodiments (not shown), the distal end 78 of the deflection wire 76 is attached to the cryo-tip 46 instead of the distal end 38 of the distal tube 34. As further shown in FIG. 3, the attachment can be accomplished by indenting a portion of the distal tube 34 to create a nest between two axially adjacent slits 60 and then bonding or welding the wire 76 to the nest. As best appreciated with cross-reference to FIGS. 3 and 4, a central portion of the wire 76 is located within a sheath spring 80 (see also FIG. 6) having a distal end 82 which is attached to the proximal tube 40 near its distal end 44. As further shown in FIG. 4, the attachment is accomplished by indenting a portion of the proximal tube 40 and then bonding or welding the sheath spring 80 to the indented portion of the proximal tube 40.

Figure 7:
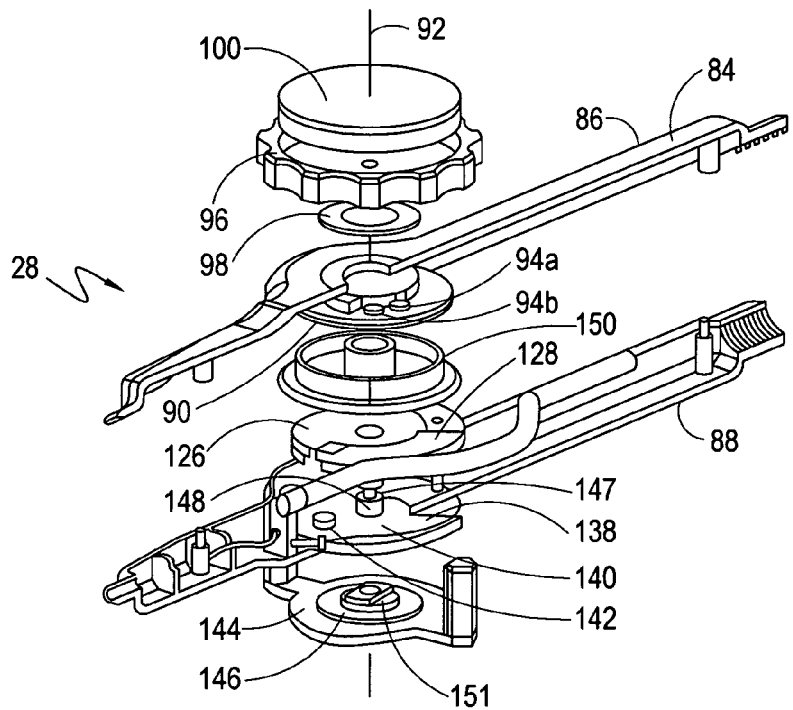
FIG. 7 is an exploded, perspective view of the catheter handle shown in FIG. 1.

From their respective distal ends 78, 82, the wire 76 and sheath spring 80 pass through the tubes 34, 40 and through the catheter body 26 (see also FIG. 5) to the handle 28 (see FIGS. 1 and 7). As shown in FIG. 7, the handle 28 includes a handle housing 84 having a handle top 86 and handle bottom 88. A generally disk shaped hoop reel 90 is positioned in and attached to the handle housing 84 to allow the hoop reel 90 to rotate about a rotation axis 92 relative to the housing 84. Although not shown, it is intended that the proximal end of the wire 76 will be partially wound around the hoop reel 90 and attached thereto using the attachment screws 94a,b. As shown, the screws 94a,b are located at a radial distance from the rotation axis 92. Also, the proximal end of the sheath spring 80 is attached to a ferrule (not shown) which is then fixedly attached to the handle top 86. With the above-described cooperation of structure, the hoop reel 90 can be rotated relative to the handle housing 84 to axially retract the deflection wire 76 and transform the distal tube 34.

Continuing with FIG. 7, it can be seen that the handle 28 includes a user operable knob 96, a friction washer 98 and a cosmetic cover 100 that are each positioned outside the handle housing 84 and centered on the rotation axis 92. As shown, the friction washer 98 is interposed between the handle top 86 and the knob 96. A screw (not shown) is provided to clamp the knob 96 toward the hoop reel 90 at a preselected clamping pressure. As a consequence, the friction washer 98 and the wall of the handle top 86 are sandwiched between the knob 96 and reel 90. With this structural arrangement, the user operable knob 96 can be rotated to selectively pull or release the deflection wire 76 (see FIG. 3), while the friction washer 98 holds the knob 96 in place after a preselected rotation. This allows the operator to release the knob 96 while maintaining a preselected deflection in the section 22 (see FIG. 1).

Figure 8:
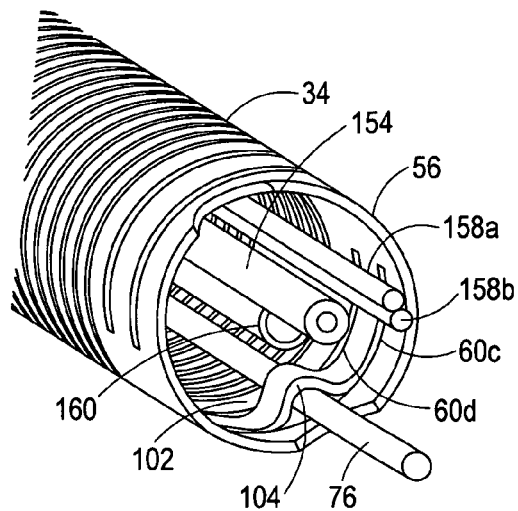
FIG. 8 is an enlarged, perspective view showing a section through the distal tube to illustrate an indentation for guiding a deflection wire.

Referring now to FIG. 8, it can be seen that within the distal tube 34, a guiding mechanism is provided to maintain the deflection wire 76 along the inner wall 102 of the distal tube 34 during axial retraction of the deflection wire 76. Specifically, as illustrated in FIG. 8, a plurality of indentations, such as indentation 104 shown, can be formed in the laser cut distal tube 34 to establish the guiding mechanism. Specifically, as shown, each indentation 104 can be formed in the wall 56 between a pair of axially adjacent slits, such as first slits 60c and 60d. Also shown, each indentation 104 forms a passageway that can be used to thread the deflection wire 76 though the indentation 104 to allow axial movement of the wire 76 relative to the indentation 104. In a typical embodiment of the cryo-catheter 20, approximately 5-15 axially spaced indentations 104 are used to maintain the deflection wire 76 along the inner wall 102 of the distal tube 34.

Figures 9A, 9B, 9C, 9D, 9E:
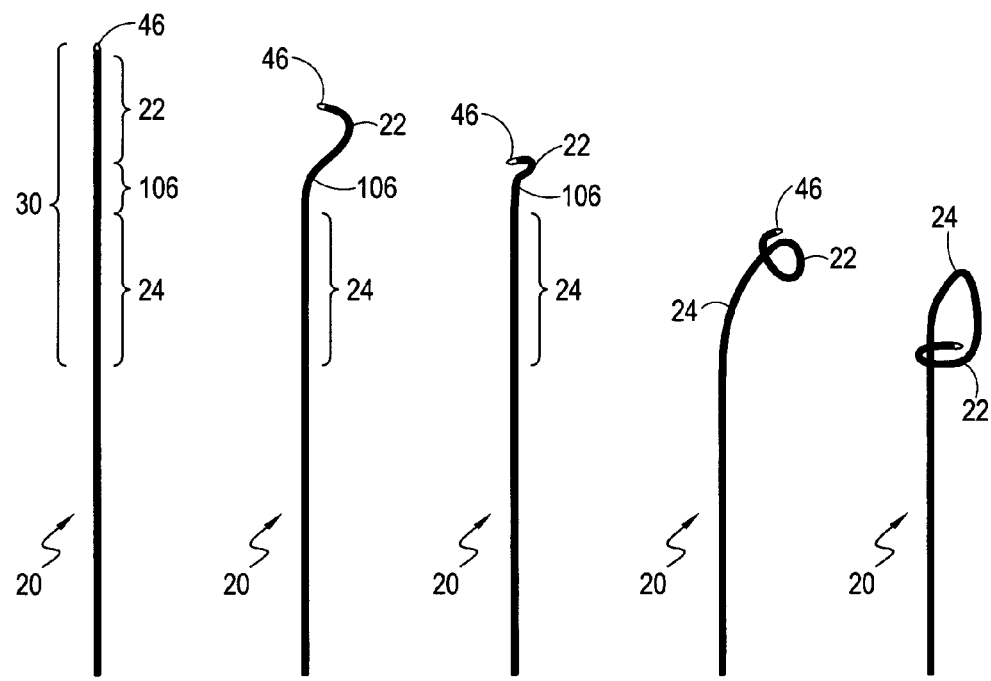
FIGS. 9A-E are a series of perspective views showing a distal portion of the cryo-catheter in various states of deflection.

The deflection of section 22 of the cryo-catheter 20 can best be appreciated with initial reference to FIG. 9A which shows the hoop section 22, bi-directional section 24 and transition section 106, all in a relaxed, undeflected state. FIG. 9B shows the cryo-catheter 20 after an initial retraction of the deflection wire 76. Comparing FIG. 9B with FIG. 9A, it can be seen that the initial retraction of the deflection wire 76 imparts a curvature to the hoop section 22 and the transition section 106. As shown in FIG. 9C, further retraction of the deflection wire 76 configures section 22 of the cryo-catheter 20 into a planar, hoop shaped configuration and imparts a curvature to the transition section 106. As best seen in FIG. 9C, the transition section 106 and the hoop section 22 deflect in different planes.

Figure 6:
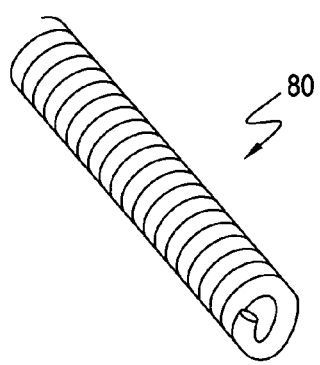
FIG. 6 is an enlarged, perspective view of a sheath spring.
Figure 10:
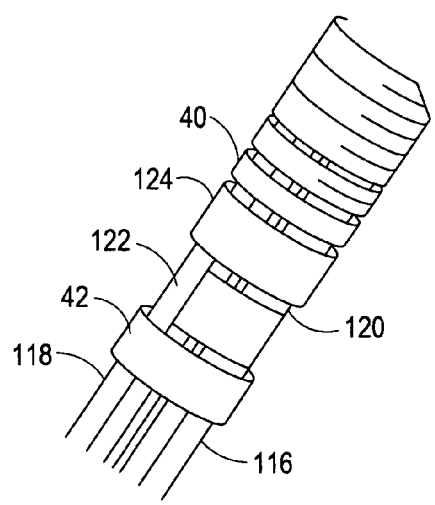
FIG. 10 is an enlarged, perspective view of the proximal end of the proximal tube.

To deflect the bi-directional section 24 (see FIG. 1), the cryo-catheter 20 includes pull wires 108, 110 having respective distal ends 112, 114 that are each attached to the proximal tube 40 near the distal end 44 of the proximal tube 40, as shown in FIG. 4. As further shown, the attachment points are located approximately one hundred eighty degrees apart around the circumference of the proximal tube 40. Also shown in FIG. 4, the attachment is accomplished by indenting a portion of the proximal tube 40 to create a nest between two axially adjacent slits and then bonding or welding the pull wires 108, 110 to the nest. As best appreciated with cross-reference to FIGS. 4 and 10, a central portion of each pull wire 108, 110 is located within a respective sheath spring 116, 118 (see also FIG. 6) having a respective distal end 120, 122 which is attached to the proximal tube 40 near its proximal end 42. As further shown in FIG. 10, the attachment is accomplished by indenting portions of the proximal tube 40 and then bonding or welding the respective sheath springs 116, 118 to the indented portion of the proximal tube 40. Note also from FIG. 10 that a portion of the proximal tube 40 distal to the nest can be slightly indented to form a distal abutment 124 for the sheath spring 118. For simplicity, sheath springs 80, 116 and 118 have been shown as simple tubes in FIGS. 4 and 10 and the actual helical structure of an exemplary sheath spring 80 is shown in FIG. 6.

From their respective distal ends 112, 114, 120, 122, the pull wires 108, 110 and sheath springs 116, 118 pass through the proximal tube 40 and through the catheter body 26 (see also FIG. 5) to the handle 28 (see FIGS. 1 and 7). A guiding mechanism can be provided to maintain each pull wire 108, 110 along the inner wall of the proximal tube 40 during an axial retraction of one of the pull wires 108, 110. Specifically, the guiding mechanism can be similar to the guiding mechanism described above for guiding the deflection wire 76 within the distal tube 34, as illustrated in FIG. 8. More specifically, a plurality of indentations can be formed in the laser cut proximal tube 40 to establish the guiding mechanism.

Figure 11A:
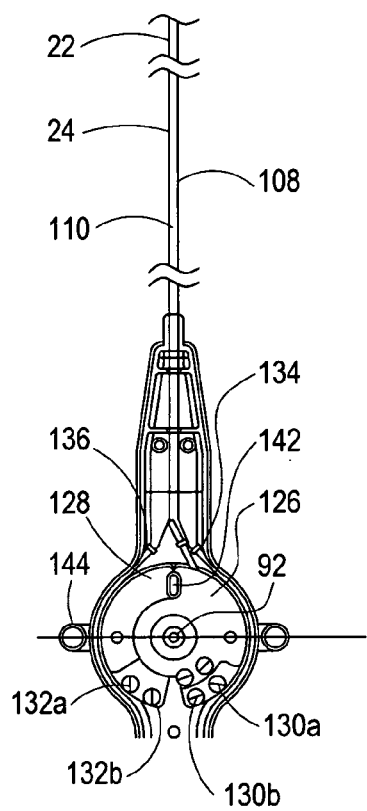
FIGS. 11A-E are a series of top plan views of the catheter handle (with the handle top removed) showing the bi-directional section of the catheter in various states of deflection.

As shown in FIG. 7, the handle 28 includes a clockwise (CW) reel 126 and a counter-clockwise (CCW) reel 128 that are positioned in and attached to the handle housing 84 to allow the reels 126, 128 to rotate about the rotation axis 92 relative to the housing 84. Although it is not shown in FIG. 7, it is to be appreciated that in use, the proximal end of the pull wire 108 is partially wound around the CW reel 126 and attached thereto using the attachment screws 130a,b (see FIG. 11A). Similarly, it is to be appreciated that the proximal end of the pull wire 110 will be partially wound around the CCW reel 128 and attached thereto using the attachment screws 132a,b (see FIG. 11A). As best seen in FIG. 11A, the screws 130a,b and 132a,b are each located at a radial distance from the rotation axis 92. For the cryo-catheter 20, the proximal end of sheath spring 116 is attached to a ferrule 134 which is then fixedly attached to the handle bottom 88. Similarly, the proximal end of sheath spring 118 is attached to a ferrule 136 which is then fixedly attached to the handle bottom 88. With this arrangement, the CW reel 126 can be rotated clockwise about the rotation axis 92 to selectively pull the pull wire 108 and the CCW reel 128 can be rotated counter-clockwise about the rotation axis 92 to selectively pull the pull wire 110.

As further shown in FIG. 7, the handle 28 includes a drive cog 138 having a drive wheel 140 that is formed with a protruding cog 142. As shown, the drive cog 138 is positioned in and attached to handle housing 84 for rotation about the rotation axis 92. Cross-referencing FIGS. 7 and 11A, it can be seen that when the cog 142 is rotated in a clockwise rotation direction it engages and rotates the CW reel 126 and when the cog 142 is rotated in the counter-clockwise rotation direction it engages and rotates the CCW reel 128. FIG. 7 further shows that each reel 126, 128 and the drive wheel 140 are stacked along the rotation axis 92 and positioned inside the handle housing 84 opposite a user operable turn knob 144 that is positioned outside the handle housing 84. A friction washer 146 is interposed between the handle bottom 88 and the knob 144. A screw 147 is then used to clamp the knob 144 toward the drive wheel 140 at a preselected clamping pressure. As a consequence, the friction washer 146 and the wall of the handle bottom 88 are sandwiched between the turn knob 144 and drive wheel 140. With this structural arrangement, the user operable turn knob 144 can be rotated to selectively retract either pull wire 108, 110, while the friction washer 146 "locks" the knob 144 in place after a preselected rotation. This allows the operator to release their hand from the knob 144 while maintaining a preselected tip deflection.

Continuing with FIG. 7, it can be seen that the drive cog 138 is formed with a spacer hub 148 to allow the reels 126, 128 to rotate after clamping the drive wheel 140 to the knob 144. In addition, a washer 150 is interposed between the reels 126, 128 and the hoop reel 90 to allow the hoop reel 90 to rotate independently of the reels 126, 128. A flat 151 formed on the knob 144 engages a corresponding flat (not shown) on the drive wheel 140 such that the knob 144 and drive wheel 140 rotate together.

In the present invention, the drive cog 138, drive wheel 140, protruding cog 142, turn knob 144, friction washer 146, and screw 147 cooperate to operate the CW reel 126 and the CCW reel 128. Specifically, they serve as means operable on the reels 126 and 128 for applying tension to the first pull wire 108 to deflect the catheter structure distal end 44 in the first direction. Thereafter, they delay an application of tension to the second pull wire 110 until at least a portion of the tension on the first pull wire 108 is selectively released. Upon application of tension to the second pull wire 110, the catheter structure distal end 44 is deflected from the first direction to the second direction.

Figure 11B:
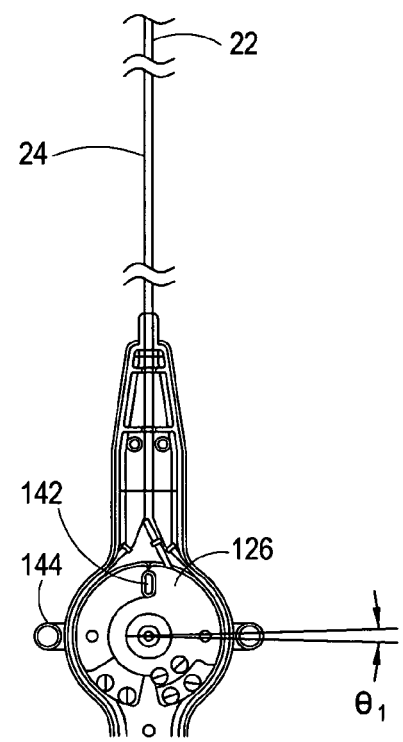

Operation of the bi-directional system for deflecting section 24 of the cryo-catheter 20 can best be appreciated with reference to FIGS. 11A-E. Beginning with FIG. 11A, the system is shown with the section 24 in the undeflected or neutral state. In this state, there is no applied tension to either pull wire 108, 110. As further shown in FIG. 11A, in the neutral state, the cog 142 is positioned between the CW reel 126 and CCW reel 128 with a gap between the cog 142 and reels 126, 128. Thus, as best seen in FIG. 11B, the user operable knob 144 must be rotated through a small angle, $\theta_1$, before the cog 142 contacts and engages the CW reel 126. The functionality of the gap will be described in greater detail below.

Figure 11C:
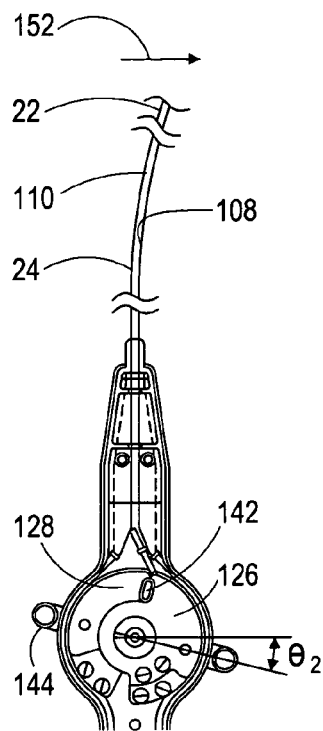

FIG. 11C shows the cryo-catheter 20 after a rotation of user operable knob 144 through an angle, $\theta_2$. It can be seen by comparing FIG. 11C with FIG. 11B that rotation of the knob 144 through an angle, $\theta_2$, causes the knob 144 to engage the CW reel 126 and rotate the CW reel 126 in a clockwise direction. This action, in turn, retracts the pull wire 108 and deflects section 24 of the cryo-catheter 20 in a first direction as indicated by arrow 152, as shown. The deflection of the section 24 pulls the pull wire 110 distally, which in turn rotates the CCW reel 128 clockwise as shown. However, it can be seen from FIG. 11C that a gap is still present between the cog 142 and the CCW reel 128.

Figure 11D:
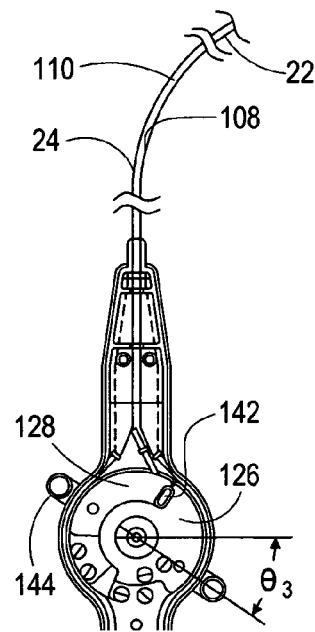

FIG. 11D shows the cryo-catheter 20 after a rotation of user operable knob 144 through an angle, $\theta_3$. This action, in turn, causes a further rotation of the CW reel 126 in a clockwise direction, further retracts the pull wire 108 and deflects section 24 of the cryo-catheter 20 to a greater extent. The increased deflection of the section 24 pulls the pull wire 110 distally, which in turn rotates the CCW reel 128 clockwise as shown. However, the initial gap (see FIG. 11A) is sized large enough so that the clockwise rotation of the CCW reel 128, due to the pull wire 110, does not cause the CCW reel 128 to engage and rotate the cog 142.

Figure 11E:
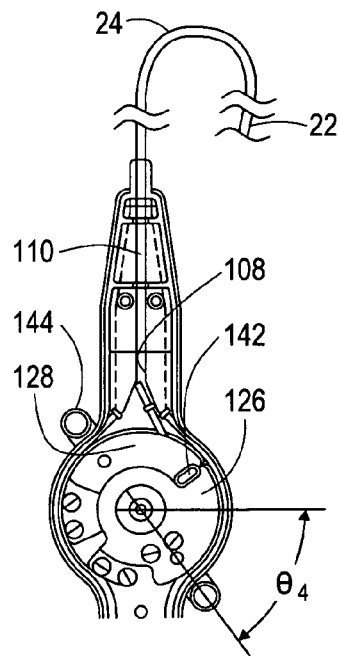

FIG. 11E shows the cryo-catheter 20 after a rotation of user operable knob 144 through an angle, $\theta_4$, that is equal to approximately forty-five degrees. This rotation of the knob 144 results in a deflection of the section 24 that is approximately equal to one hundred-eighty degrees, as shown. FIG. 11E further shows that a gap is present between the cog 142 and the CCW reel 128. From the above description, it is apparent that the CCW reel 128 does not engage or apply a force on the cog 142 during a rotation of the knob 144 from the neutral position (FIG. 11A) to the position shown in FIG. 11E. It follows that when the knob 144 is rotated counter-clockwise from the position shown in FIG. 11E to the neutral position (FIG. 11A) that the cog 142 does not engage the CCW reel 128. Specifically, due to the gap between the cog 142 and reels 126, 128, the pull wire 110 is not pulled distally by the CCW reel 128 as the tension in the pull wire 108 is released. This allows the section 24 to smoothly recover from large deflections such as the large deflection shown in FIG. 11E. Moreover, FIG. 11A shows that the bi-directional system of the cryo-catheter 20 is functionally symmetric and accordingly it can be expected that a counter-clockwise rotation of the cog 142 will result in a deflection of the section 24 in a direction opposite to arrow 152 shown in FIG. 11C.

The deflection of bi-directional section 22 can also be appreciated with reference to FIGS. 9C-9E and FIG. 1. Beginning with FIG. 9C, the cryo-catheter 20 is shown with the hoop section 22 and transition section 106 deflected and the bi-directional section 22 in a relaxed, undeflected state. FIG. 9D shows the cryo-catheter 20 after an initial retraction of the pull wire 108 (see also FIG. 11D). As shown in FIG. 9E, further retraction of the pull wire 108 results in a deflection of the section 24 that is approximately equal to one hundred-eighty degrees, in a first direction as indicated by arrow 152. FIG. 1 shows the bi-directional section after the pull wire 108 has been released and the pull wire 110 has been pulled distally by the CCW reel 128. This transition from FIG. 11E to FIG. 1 is accomplished by moving the knob 144 counterclockwise approximately ninety degrees. Comparing FIGS. 11A-E to FIG. 1, it can be seen that the bi-directional section 24 in FIG. 1 has been deflected in a direction that is opposite and coplanar to the direction of arrow 152.

Figure 5:
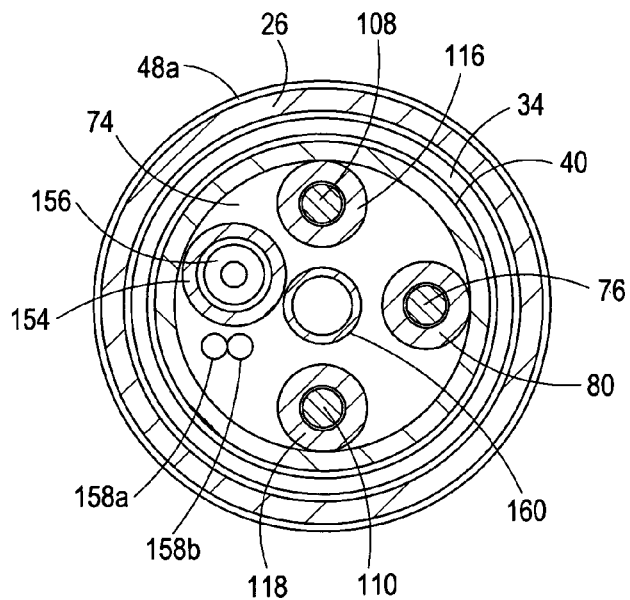
FIG. 5 is a cross-sectional view as seen along line 5-5 in FIG. 1, showing the distal portion of the cryo-catheter in a relaxed, undeflected state.

FIGS. 5 and 8 also show that the cryo-catheter 20 includes a refrigerant supply line having a supply tube 154 and a capillary tube 156, with the capillary tube 156 attached to the distal end of the supply tube 154. With this combination, an extracorporeally located refrigerant supply unit (not shown) can be activated to introduce a regulated flow of refrigerant into the supply tube 154 for subsequent flow through the capillary tube 156. From the capillary tube 156, the refrigerant expands into the cryo-tip 46 (FIG. 1), or if desired into the hoop section 22, or both, absorbing heat as it expands. A return line is provided to exhaust expanded refrigerant. For the embodiment shown, the return line is established in the volume between the supply line and catheter body 26. FIG. 8 also shows that thermocouple wires 158a,b are provided to measure a cryo-tip 46 temperature. A pressure monitoring line 160, which typically extends from the cryo-tip 46 to an extracorporeally located pressure gauge (not shown) is provided to measure a pressure within the cryo-tip 46.

In one application of the cryo-catheter 20, the cryo-tip 46, hoop section 22 and bi-directional section 24 are introduced into the left atrium through an introducer sheath (not shown) using a trans-septum approach. Once in the left atrium, section 22 is deflected into a hoop shape or partial hoop shape. Next, part or all of the deflected section 22 is placed into contact with target tissue which is typically peripheral tissue surrounding an ostium where a pulmonary vein connects with the left atrium. Deflection of the bi-directional section 24 can be used to achieve the desired contact between the hoop section 22 and the target tissue. Once adequate contact is made, refrigerant is expanded in the cryo-tip 46, hoop section 22 (or both) until an adequate lesion has been created. Sections 22, 24 of the cryo-catheter 20 can then be re-configured to contact other targeted tissue or removed from the vasculature to complete the procedure.

While the particular System for Bi-Directionally Controlling the Cryo-tip of a Cryoablation Catheter and corresponding methods of preparation and use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for steering a catheter through the vasculature of a patient using bi-directional control, said system comprising:
    a tubular catheter structure having a proximal end and a distal end, wherein said tubular catheter structure includes a tube having a wall with an inner surface, wherein said wall is formed with a plurality of slits to define a plurality of axially-spaced wall portions separated by said slits, and wherein a plurality of non-adjacent wall portions are indented to form a first passageway along the inner surface and a plurality of non-adjacent wall portions are indented to form a second passageway along the inner surface;
    a clockwise (CW) reel;
    a first pull wire positioned in the first passageway and having a first end attached to said catheter structure and a second end attached to said CW reel, said first pull wire for deflecting said catheter structure distal end in a first direction in response to a rotation of said CW reel about a rotation axis, wherein said first passageway maintains said first pull wire along said inner wall during a movement of said first pull wire;
    a counterclockwise (CCW) reel;
    a second pull wire positioned in the second passageway and having a first end attached to said catheter structure and a second end attached to said CCW reel, said second pull wire for deflecting said catheter structure distal end in a second direction in response to a rotation of said CCW reel about the rotation axis, with the second direction being substantially coplanar and opposite to the first direction, wherein said second passageway maintains said second pull wire along said inner wall during a movement of said second pull wire; and
    a means operable on said CW and CCW reels for applying a tension to said first pull wire to deflect said catheter structure distal end in the first direction and thereafter for delaying an application of tension to said second pull wire until at least a portion of said tension on said first pull wire is selectively released to respectively deflect said catheter structure distal end from the first direction to the second direction.

2. A system as recited in claim 1 wherein said tube is transformable between a first, relaxed configuration wherein said tube is substantially cylindrical shaped and a second, deflected configuration.

3. A system as recited in claim 1 wherein said tube is made of a metal.

4. A system as recited in claim 3 wherein said first passageway is diametrically opposed from said second passageway.

5. A system as recited in claim 4 wherein between approximately 5 to 15 non-adjacent wall portions are indented to form said first passageway for threading said first pull wire therethrough.

6. A system as recited in claim 1 further comprising a catheter handle having a handle housing, and wherein said CW reel is attached to said housing for rotation relative to said housing about the rotation axis in a first rotation direction to pull said first pull wire and a CCW reel attached to said housing for rotation relative to said housing about the rotation axis in a second rotation direction to pull said second pull wire, with said first rotation direction being opposite said second rotation direction.

7. A system as recited in claim 6 wherein said handle further comprises:
    a drive cog mounted on said handle housing for rotation about the rotation axis, said drive cog for engaging said CW reel to rotate said CW reel in the first rotation direction;
    a turn knob mounted on said handle housing for rotation about the rotation axis, said turn knob for selectively rotating said drive cog about the rotation axis; and
    a friction washer for holding said turn knob in a selected position relative to said handle housing to maintain a preselected tension in said first pull wire.

8. A system as recited in claim 7 wherein said friction washer is clamped between said turn knob and said handle housing at a preselected clamping pressure.

9. A system as recited in claim 7 wherein said drive cog is engageable with said CCW reel to rotate said CCW reel in the second rotation direction.

10. A system for steering a catheter through the vasculature of a patient using bi-directional control, said system comprising:
    a tubular catheter structure having a proximal end and a distal end, wherein said tubular catheter structure includes a tube having a wall with an inner surface, wherein said wall is formed with a plurality of slits to define a plurality of axially-spaced wall portions separated by said slits, and wherein a plurality of non-adjacent wall portions are indented to form a first passageway along the inner surface and a plurality of non-adjacent wall portions are indented to form a second passageway along the inner surface, and wherein said tube is transformable between a first, relaxed configuration wherein said tube is substantially cylindrical shaped and a second, deflected configuration;

a catheter handle having a handle housing and connected to said proximal end of said tubular catheter structure;

a clockwise (CW) reel attached to said handle housing for rotation relative to said handle housing about a rotation axis in a first rotation direction;

a first pull wire positioned in the first passageway and having a first end attached to said catheter structure and a second end attached to said CW reel, said first pull wire for deflecting said catheter structure distal end in a first direction in response to a rotation of said CW reel about the rotation axis, wherein said first passageway maintains said first pull wire along said inner wall during a movement of said first pull wire;

a counterclockwise (CCW) reel attached to said housing for rotation relative to said housing about the rotation axis in a second rotation direction opposite said first rotation direction;

a second pull wire positioned in the second passageway and having a first end attached to said catheter structure and a second end attached to said CCW reel, said second pull wire for deflecting said catheter structure distal end in a second direction in response to a rotation of said CCW reel about the rotation axis, with the second direction being substantially coplanar and opposite to the first direction, wherein said second passageway maintains said second pull wire along said inner wall during a movement of said second pull wire; and a drive cog mounted on said handle housing for rotation about the rotation axis, said drive cog operable on said CW and CCW reels for applying a tension to said first pull wire to deflect said catheter structure distal end in the first direction and thereafter for delaying an application of tension to said second pull wire until at least a portion of said tension on said first pull wire is selectively released to respectively deflect said catheter structure distal end from the first direction to the second direction.

11. A system as recited in claim 10 wherein said first passageway is diametrically opposed from said second passageway.

12. A system as recited in claim 11 wherein between approximately 5 to 15 non-adjacent wall portions are indented to form said first passageway for threading said first pull wire therethrough.

13. A system as recited in claim 12 wherein between approximately 5 to 15 non-adjacent wall portions are indented to form said second passageway for threading said second pull wire therethrough.

14. A system as recited in claim 10 further comprising:

a turn knob mounted on said handle housing for rotation about the rotation axis, said turn knob for selectively rotating said drive cog about the rotation axis; and a friction washer clamped between said turn knob and said handle housing at a preselected clamping pressure for holding said turn knob in a selected position relative to said handle housing to maintain a preselected tension in said first pull wire.

* * * * *